(12) United States Patent
Johnson et al.

(10) Patent No.: US 8,858,185 B2
(45) Date of Patent: Oct. 14, 2014

(54) FLUID FLOW RATE COMPENSATION SYSTEM USING AN INTEGRATED CONDUCTIVITY SENSOR TO MONITOR TUBING CHANGES

(75) Inventors: Thomas D. Johnson, Gurnee, IL (US); Ryan R. Brumund, Libertyville, IL (US); James A. McNeely, Buffalo Grove, IL (US)

(73) Assignee: Hospira, Inc., Lake Forest, IL (US)

(*) Notice: Subject to any disclaimer, the term of this patent is extended or adjusted under 35 U.S.C. 154(b) by 577 days.

(21) Appl. No.: 13/165,490

(22) Filed: Jun. 21, 2011

(65) Prior Publication Data

US 2011/0318198 A1   Dec. 29, 2011

Related U.S. Application Data

(60) Provisional application No. 61/357,660, filed on Jun. 23, 2010.

(51) Int. Cl.
| | |
|---|---|
| *F04B 49/06* | (2006.01) |
| *F04B 43/12* | (2006.01) |
| *A61M 1/00* | (2006.01) |
| *F04B 43/00* | (2006.01) |
| *A61M 5/168* | (2006.01) |

(52) U.S. Cl.
CPC ............. *F04B 43/12* (2013.01); *F04B 43/0072* (2013.01); *F04B 49/065* (2013.01); *F04B 43/0081* (2013.01); *A61M 5/168* (2013.01)
USPC .................... 417/44.1; 417/44.11; 417/477.7; 604/153

(58) Field of Classification Search
CPC .... F04B 43/12; F04B 43/0081; F04B 49/065; F04B 43/0072; A61M 5/168
USPC ........... 417/477.9, 477.7, 477.12, 477.3, 474, 417/44.11, 44.1; 604/153; 73/1.36
See application file for complete search history.

(56) References Cited

U.S. PATENT DOCUMENTS

| | | | | |
|---|---|---|---|---|
| 4,039,269 | A | * | 8/1977 | Pickering ...................... 417/475 |
| 4,105,028 | A | * | 8/1978 | Sadlier et al. ................... 604/65 |
| 4,210,138 | A | * | 7/1980 | Jess et al. ......................... 604/67 |
| 4,432,699 | A | * | 2/1984 | Beckman et al. ............... 417/63 |
| 4,453,931 | A | | 6/1984 | Pastrone |
| 4,617,014 | A | * | 10/1986 | Cannon et al. ................... 604/67 |
| 4,690,673 | A | * | 9/1987 | Bloomquist ..................... 604/67 |
| 4,702,675 | A | | 10/1987 | Aldrovandi et al. |

(Continued)

FOREIGN PATENT DOCUMENTS

| | | |
|---|---|---|
| EP | 501234 B1 | 9/1992 |
| EP | 2 381 260 | * 10/2011 |

(Continued)

*Primary Examiner* — Devon Kramer
*Assistant Examiner* — Lilya Pekarskaya
(74) *Attorney, Agent, or Firm* — Michael R. Crabb (57) ABSTRACT

An infusion system and method for controlling the fluid flow from a pump includes a pump system that has a controller that utilizes an algorithm to control the flow rate of fluid through tubing. A plurality of electrodes operatively contacts an electrically conductive portion of the tubing that is also acted upon by the pump system. The electrodes monitor electrical properties of the tubing and provide an electric signal indicative thereof to the controller, which varies the flow rate of the fluid through the tubing as a result of the electric signal.

20 Claims, 10 Drawing Sheets

(56) References Cited

U.S. PATENT DOCUMENTS

| | | | | |
|---|---|---|---|---|
| 4,950,244 | A | 8/1990 | Fellingham | |
| 5,018,945 | A * | 5/1991 | D'Silva | 417/12 |
| 5,049,047 | A | 9/1991 | Polaschegg et al. | |
| 5,103,211 | A * | 4/1992 | Daoud et al. | 340/608 |
| 5,180,287 | A | 1/1993 | Natwick et al. | |
| 5,215,450 | A | 6/1993 | Tamari | |
| 5,319,979 | A | 6/1994 | Abrahamson | |
| 5,464,392 | A | 11/1995 | Epstein et al. | |
| 5,522,799 | A * | 6/1996 | Furukawa | 604/65 |
| 5,586,868 | A | 12/1996 | Lawless et al. | |
| 5,657,000 | A | 8/1997 | Ellingboe | |
| 5,661,245 | A | 8/1997 | Svoboda et al. | |
| 5,695,473 | A | 12/1997 | Olsen | |
| 5,733,257 | A | 3/1998 | Sternby | |
| 5,803,712 | A * | 9/1998 | Davis et al. | 417/45 |
| 5,935,106 | A | 8/1999 | Olsen | |
| 6,164,921 | A | 12/2000 | Moubayed et al. | |
| 6,347,553 | B1 | 2/2002 | Morris et al. | |
| 6,497,680 | B1 | 12/2002 | Holst et al. | |
| 6,719,535 | B2 * | 4/2004 | Rakestraw et al. | 417/50 |
| 6,857,318 | B1 | 2/2005 | Silber et al. | |
| 7,104,763 | B2 | 9/2006 | Bouton et al. | |
| 7,104,769 | B2 | 9/2006 | Davis | |
| 7,291,123 | B2 | 11/2007 | Baraldi et al. | |
| 7,360,999 | B2 | 4/2008 | Nelson et al. | |
| 7,397,166 | B1 * | 7/2008 | Morgan et al. | 310/328 |
| 7,785,284 | B2 | 8/2010 | Baraldi et al. | |
| 8,226,597 | B2 * | 7/2012 | Jacobson et al. | 604/67 |
| 8,347,731 | B2 * | 1/2013 | Genosar | 73/861.08 |
| 2004/0253123 | A1 * | 12/2004 | Xie et al. | 417/410.1 |
| 2004/0254513 | A1 * | 12/2004 | Shang et al. | 604/5.01 |
| 2005/0209563 | A1 | 9/2005 | Hopping et al. | |
| 2005/0214129 | A1 | 9/2005 | Greene et al. | |
| 2005/0238506 | A1 | 10/2005 | Mescher et al. | |
| 2006/0002799 | A1 | 1/2006 | Schann et al. | |
| 2006/0275142 | A1 | 12/2006 | Bouton et al. | |
| 2008/0188789 | A1 | 8/2008 | Galavotti et al. | |
| 2010/0069892 | A1 | 3/2010 | Steinbach et al. | |
| 2010/0211002 | A1 * | 8/2010 | Davis | 604/67 |

FOREIGN PATENT DOCUMENTS

| | | |
|---|---|---|
| EP | 2381260 A2 * | 10/2011 |
| WO | 2004/0254513 U | 10/1981 |
| WO | 93/04284 | 4/1993 |
| WO | 2004/035115 A1 | 4/2004 |
| WO | 2006/016122 A1 | 2/2006 |
| WO | 2008/059492 A2 | 5/2008 |

* cited by examiner

FLUID FLOW RATE COMPENSATION SYSTEM USING AN INTEGRATED CONDUCTIVITY SENSOR TO MONITOR TUBING CHANGES

CROSS REFERENCE TO RELATED APPLICATION

This application claims the benefit of U.S. Provisional Application No. 61/357,660 filed Jun. 23, 2010.

BACKGROUND OF THE INVENTION

This invention relates to pumps for delivery of fluids to a patient. More specifically this invention relates to a fluid flow rate compensation system that monitors the tubing used in a pump in order to control the fluid flow rate of the pump or ascertain information about the fluid in the tubing.

Peristaltic pumps provide a pumping mechanism that pumps fluid through tubing by flexing or compressing the tubing repeatedly to achieve a desired flow rate. The flexing of the tubing induces wear that changes the geometric and mechanical properties of the tubing (e.g. elastic modulus, tan delta, wall thickness, diameters, etc.). These tubing properties directly impact the amount of fluid delivered in a pump stroke. Therefore by monitoring and understanding how the tubing is changing over time or over a plurality of pumping cycles, one can predict or compensate for the tubing wear which can result in improved pump performance.

One of the major factors in the peristaltic pumping flow rate is the geometry of the tubing. Because nothing can be manufactured perfectly there is a tolerance associated with the inner diameter (volume capacity) of the tubing as it comes from the manufacturer. A tolerance of +/−0.002 inches on 0.100 inches inner diameter tubing means a volume change of plus or minus 4%. For example, tubing that has an inner diameter of 0.102 inches will over deliver by 4% when it is initially used in the pump. If the pump knows the inner diameter of the tubing is 0.102 inches it can calculate the volume in the tubing, reduce the pump speed and achieve the desired flow rate.

A second geometric effect is caused by the tubing properties changing over time. It is known in polymer chemistry that as polymers degrade due to mechanical, environmental, or aging effects their polymer chains begin to break down, which results in a volume fraction decrease and increased densification. Even a piece of tubing sitting on the shelf will change over time and could affect the pump flow rate once installed in the pump. However, this effect is relatively small compared to mechanical degradation caused by the pump.

The most common technique for compensating for tubing wear is to include an algorithm in the pump that adjusts the mechanisms speed based on the amount of time the pump is running. Such an algorithm is developed based on running flow rate accuracy tests for extended periods of time. The pump is run on a single set mechanism speed and data is collected over time to show how the flow rate is affected as a function of time. This process is repeated over several set mechanism speeds such that a full characterization on how flow rate is affected by tubing wear. Once this data is obtained, an algorithm can be developed. Typically, for a given mechanism speed, flow rate begins to diminish over time as tubing wears. In order to compensate for this effect, the algorithm would adjust the mechanism speed (e.g. increase speed) such that steady flow rate could be maintained over time.

Several algorithms are known in the art. Nose et al., U.S. Pat. No. 7,284,956 describes in general one such invention using any number of feedback controllers, mechanism, sensors to maintain a pump flow rate at its operating set point. Another algorithm, specific to peristaltic pumping that is well known in the art is to utilize the internal pressure profiles which exist in the tubing.

Another technique for compensating for tubing wear is to implement sensors that characterize the fluid flow directly or indirectly and put it into a control system for closed loop feedback. Among the most common sensors that have been proposed for this are the indirect sensors. These sensors measure a characteristic that is indicative or can be correlated to the flow rate. Some of these common methods include: 1) measurement of tubing dimensions (inside diameter, outside diameter); 2) measurement of force to occlude/pump the tubing; or 3) measurement of the pressure inside/outside the tubing.

These techniques all rely on measuring properties that impact flow rate. Therefore monitoring how these properties change over time would also indicate how the flow rate is changing over time due to tubing wear. Another more rational approach is to utilize a sensor that directly indicates flow rate, a flow sensor. Many types of flow sensors exist (optical, ultrasonic, magnetic, etc). While these present one solution, many disadvantages exist for the medical device market because of the particularly high cost of implementation and clinical issues of these techniques.

Another way this problem has been overcome is to improve the tubing material itself. That is, to design and manufacture a tubing material that has reduced wear characteristics and can withstand the many cycles of compression that is undergone in peristaltic pumping. As such, materials such as silicone and Tygon™ are among the most popular for peristaltic tubing applications. As opposed to thermoplastic materials such as polyvinylchloride (PVC), they are highly resilient and compliant and have been shown to perform well in long term pump applications. Some disadvantages in this solution are the higher cost of this material, the difficulty in joining or attaching the tubing to other polymer components, and although the wear is greatly improved, the tubing still does degrade over time and is not a complete solution to the problem.

The most common current method of compensating for tubing wear in pump applications is to use an algorithm to offset the effect. In fact, many of the techniques presented are not currently known to be used in any medical pump device that is on market today.

Therefore, a principal object of the present invention is to provide an infusion system with a fluid flow rate monitoring and compensation system that improves the efficiency and accuracy of fluid flow through tubing over time.

Yet another object of the present invention is to provide a more cost effective fluid flow rate monitoring and compensation system.

Yet another object of the present invention is to utilize electrical properties of tubing to vary the flow rate of fluid through tubing.

Yet another object of the present invention is to utilize electrical properties of tubing and the fluid media flowing within the tubing to determine if there are gas or air bubbles in the fluid, breaks or leaks in the tubing.

These and other objects, features, or advantages of the present invention will become apparent from the specification and claims.

SUMMARY OF THE INVENTION

An infusion system is disclosed that monitors variations over time of properties of a section of tubing acted upon by a pump and uses a controller and algorithm to compensate for such variations to provide a consistent rate of fluid flow from the pump. A first embodiment of such an infusion system utilizes a force sensor that engages the tubing wherein an actuating device forces the force sensor against the tubing to compress the tubing. A sensing device is then provided to monitor the actuating device in order to determine characteristics of the actuating device. The sensor and sensing device are electrically connected to a controller of the pump to provide compression information regarding the tubing so that an algorithm can control the fluid flow rate through the tubing as the tubing changes over time.

In a second embodiment the infusion system presented also has a pump system that provides fluid to the patient and has a controller that utilizes an algorithm to control the flow rate of fluid through tubing. A portion of the tubing is electrically conductive and a plurality of electrodes operatively contacts the electrically conductive portion of the tubing to monitor the electrical properties of the tubing and to provide an electric signal. An electrical signal is provided to the electrodes so that they can send an electric signal to the controller. The controller can use an algorithm to operate the pump system to vary the flow rate of the fluid through the tubing as a result of the electrical properties of the tubing. Thus, as electrical properties of the tubing change over time the fluid flow rate accordingly is altered to effectively compensate for degradation or wear of the tubing over time or a number of repeated pumping cycles.

DESCRIPTION OF THE PREFERRED EMBODIMENT

Figure 9:
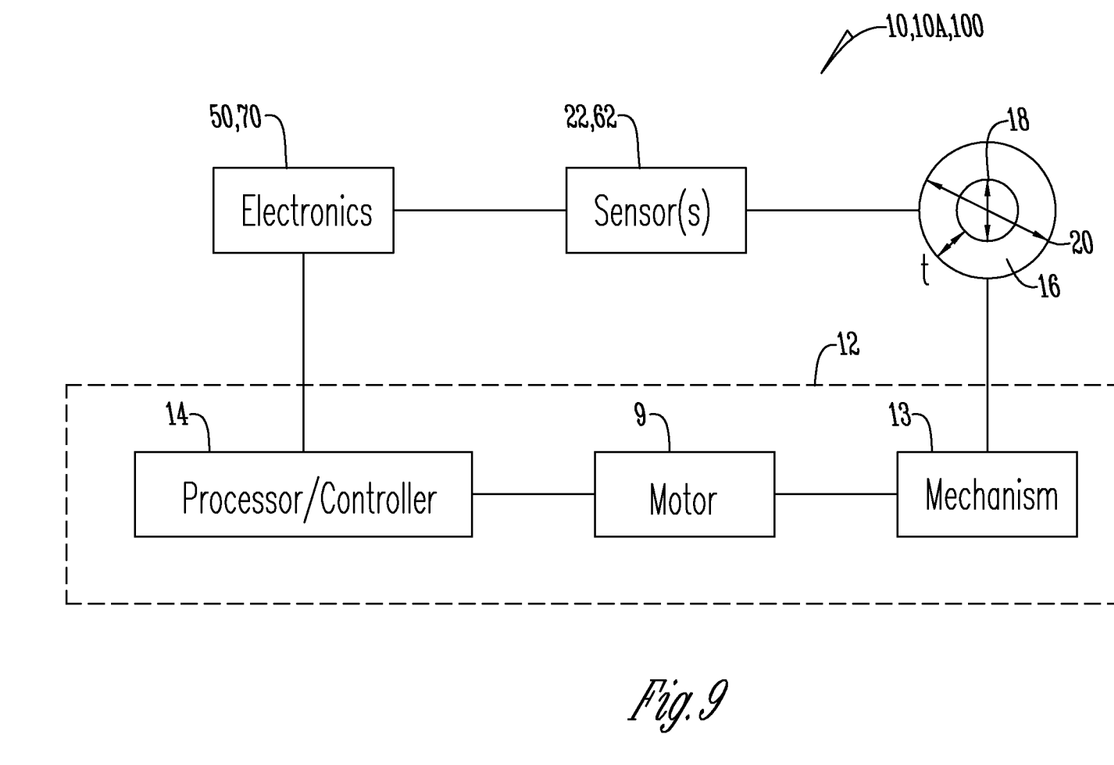
FIG. 9 is a block diagram depicting some of the components of the present invention.

The figures illustrate the invention in the context of infusion systems 10, 10A, 100; however the invention has applicability to other infusion systems and fluid handling systems as well. As generally depicted in FIG. 9, the infusion systems 10, 10A, 100 utilize a pump 12 that in one embodiment is a peristaltic pump that includes a controller 14 that contains an algorithm to adjust fluid flow by operating a motor 9 that manipulates or operatively engages via a pumping mechanism 13 a section of tubing 16 through which fluid flows. The tubing 16 can be of any shape, including the standard circular or alternatively hexagonal, square or the like. The tubing 16 has an inner diameter 18 and outer diameter 20 and in addition has a predetermined ovality, modulus of elasticity and other such inherent characteristics. The tubing 16 may be any type of material including PVC, a polymer composite, a conductive polymer composite (CPC) or the like.

Figure 1:
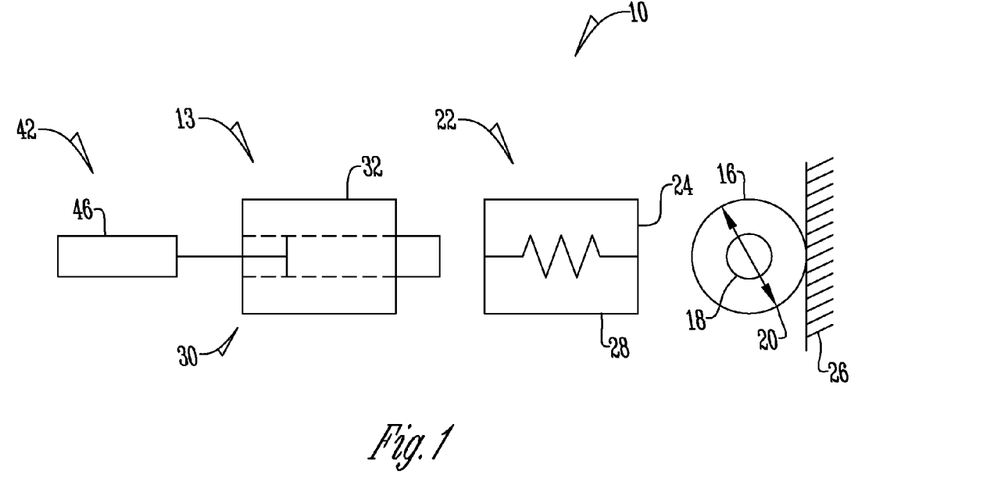
FIG. 1 is a schematic diagram depicting one embodiment of the present invention.
Figure 1A:
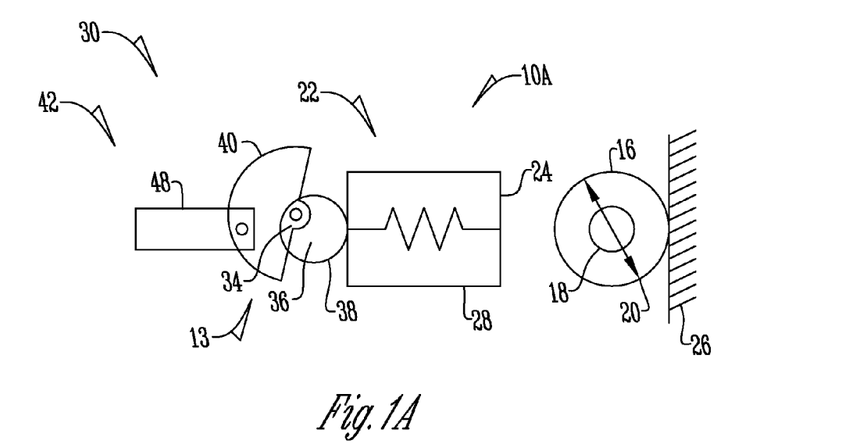
FIG. 1A is a schematic diagram of an alternative embodiment of the present invention.

FIGS. 1 and 1A show two different embodiments of infusion systems 10, 10A that are utilized to monitor the tubing 16 in order to communicate to the controller 14 of the peristaltic pump 12 so that a consistent fluid flow rate is provided through the tubing at all times. The first infusion system 10, as shown in FIG. 1, presents a force sensor 22, which is operatively associated with a finger 24 of the pumping mechanism 13 and the tubing 16, and that in a preferred embodiment is a load cell that periodically engages the tubing 16 against a hard stop 26 on the pump housing or door. The force sensor 22 can be any size or shape, specifically the length of the compression area tip can have ridges, have a round shaped tip, chiseled tip shape or the like. The force sensor 22 can also be made of any material and can be mounted on one of the fingers 24 of a pumping mechanism 13 that applies compressive pumping forces to the tubing 16.

In one embodiment this force sensor 22 is spring loaded and is held by a sensor holder 28. The force sensor 22 can be any type of force measurement device including but not limited to a flexible beam, diaphragm strength gauge, amplified/ unamplified compression readings and the like. Multiple force sensors can be used at different points along or around the tubing 16.

In the linear peristaltic embodiment shown in FIG. 1, engaging the force sensor 22 is an actuating device 30 that is a linear motion device 32 that causes linear motion to provide force on the force sensor 22. In an alternative embodiment shown in FIG. 1A, the actuating device 30 is a rotating cam shaft 34 having a cam shaft lobe 36, an eccentric 38, and a position flag 40 where the cam shaft 34 rotates to cause linear movement of the force sensor 22 against the tubing 16.

The system 10, 10A additionally has a motor position sensing device 42 for detecting the angular and/or the linear position of the actuating device 30. In the embodiment where the actuating device 30 is a linear motion device 32 the sensing device 42 is a potentiometer encoder 46. In the embodiment where the actuating device 30 is a rotating cam shaft 34 the sensing device 42 is a flag sensor 48.

The system 10, 10A is electrically connected to the pump controller 14 via electronics 50 to provide data and information accordingly. Electronics 50 for the purpose of measuring electronic signals may include any of the amplification, signal, conditioning, analog to digital conversion and power conversion.

The information is then inputted in an algorithm at the controller 14 of pump 12. D'Silva (U.S. Pat. No. 5,018,945) that is incorporated herein discloses an algorithm for adjusting the motor speed of a peristaltic pump by measuring the change in outside diameter of the tubing (Delta D). One preferred embodiment most recently was described by Silber et al. U.S. Pat. No. 6,857,318 that also is incorporated herein. This patent discloses an apparatus using force sensors to infer internal pressure information during peristaltic pumping and an algorithm to adjust pump speed accordingly. The algorithm determines precise flow rate variances for the output of the sensors and can be resident on the pump or elsewhere depending upon the application. Tube presence detection and mis-loaded set detection can additionally be provided.

In operation during each stroke the force sensor 22 or finger 24 starts fully retracted and is not touching the tubing 16. At this point in time the force is at a zero baseline. The finger 24 then moves forward until the force sensor 22 touches the tubing 16 where the force data registers the touch as a positive force value. The finger 24 then compresses the tubing 16 until the walls of the tubing 16 touch. The force data gently increases throughout the travel but is not quite linear because the geometry of the tubing 16 is changing. The finger 24 and the force sensor 22 then compress the walls of the tubing 16 slightly causing the force data to sharply rise. Specifically the finger 24 and the force sensor 22 are no longer changing the geometry of the tubing but just compressing the wall material. This is best shown by the graphs in FIGS. 2, 2A and 5.

Figure 2:
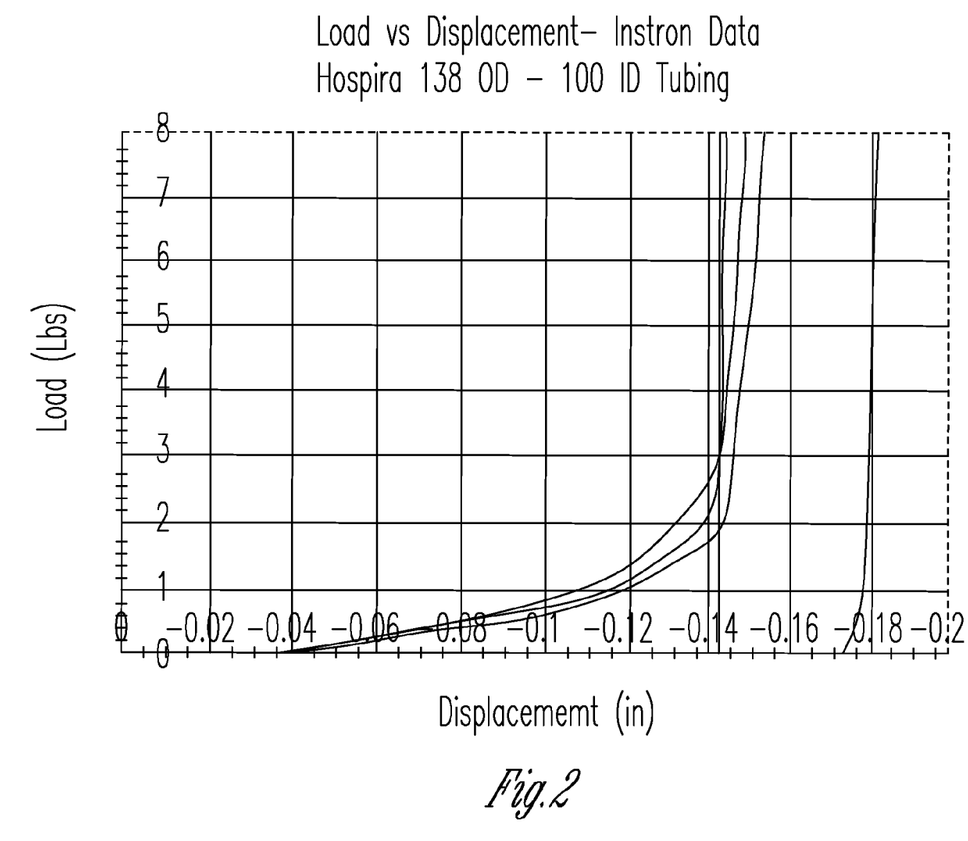
FIG. 2 is a graph of tubing compression force data from lab tests providing displacement of an actuating device that moves a force sensor against tubing on the X axis versus load on the Y axis for various tubing samples having a given set of nominal outside and inside diameters, with and without fluid present in the tubing.

FIG. 2 is a graph of tubing compression force data from lab tests providing displacement of an actuating device that moves a force sensor against tubing on the X axis versus load on the Y axis for various tubing samples having a given set of nominal outside and inside diameters, with and without fluid present in the tubing. In FIG. 2, tubing with an outside diameter of 0.138 inches and an inside diameter of 0.100 inches was utilized.

In general, FIG. 2 shows initially a no-load condition over the first 0.040 inches of actuating device travel until the actuator makes contact with the tubing. At this point, if tubing is present, the load rises linearly as the tubing deforms. Then, as the tubing occludes, (i.e. walls compress and flatten to form a rectangular cross-section) there is a 'knee' in the curves or an abrupt increase in load over a small displacement distance. Some important observations can be drawn from this graph. First, the point at which the actuator/finger contacts the outside diameter of the tubing 16 can be detected on the graph. Second, the point at which the tubing fully occludes is clearly visible on the load vs. displacement graph (i.e., the knee or sharp upturn in the curve). Third, the graph shows repeatability of this trend (over several samples) for situations where the tube is filled with liquid and where it is not filled with liquid but is empty or filled with air. For tubing filled with liquid the knee in the curve occurs at a higher force than tubing without liquid. The curve on the far right of FIG. 2 represents a run with no tubing in place. That run was done merely to verify the testing setup, wherein the actuator was positioned 0.180 inches from the hard stop surface that normally provided the resting surface for the tubing.

Figure 2A:
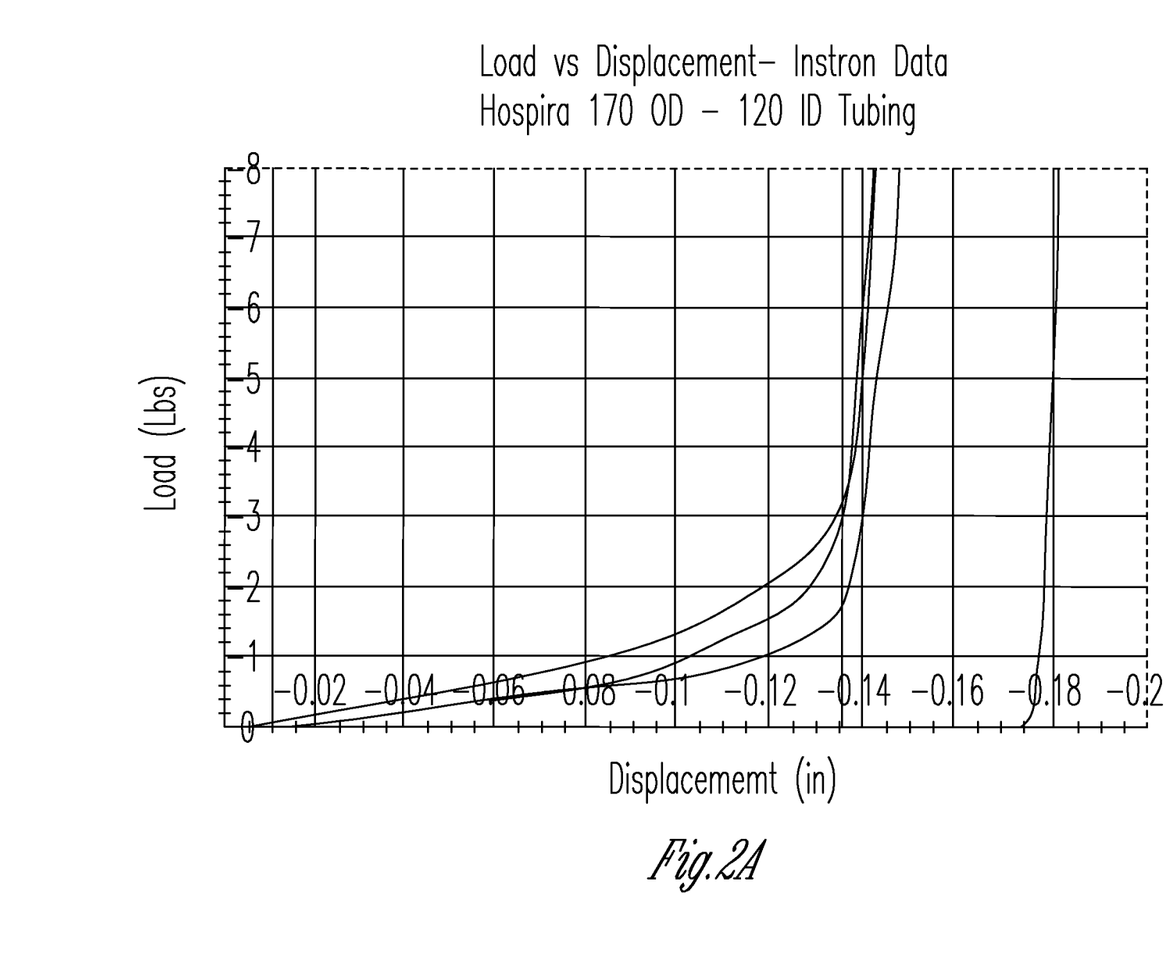
FIG. 2A is a graph of tubing compression force data from lab tests providing displacement of an actuating device that moves a force sensor against tubing on the X axis versus load on the Y axis for various tubing samples having a second given set of nominal outside and inside diameters that are different than those depicted in FIG. 2, with and without fluid present in the tubing.
Figure 3:
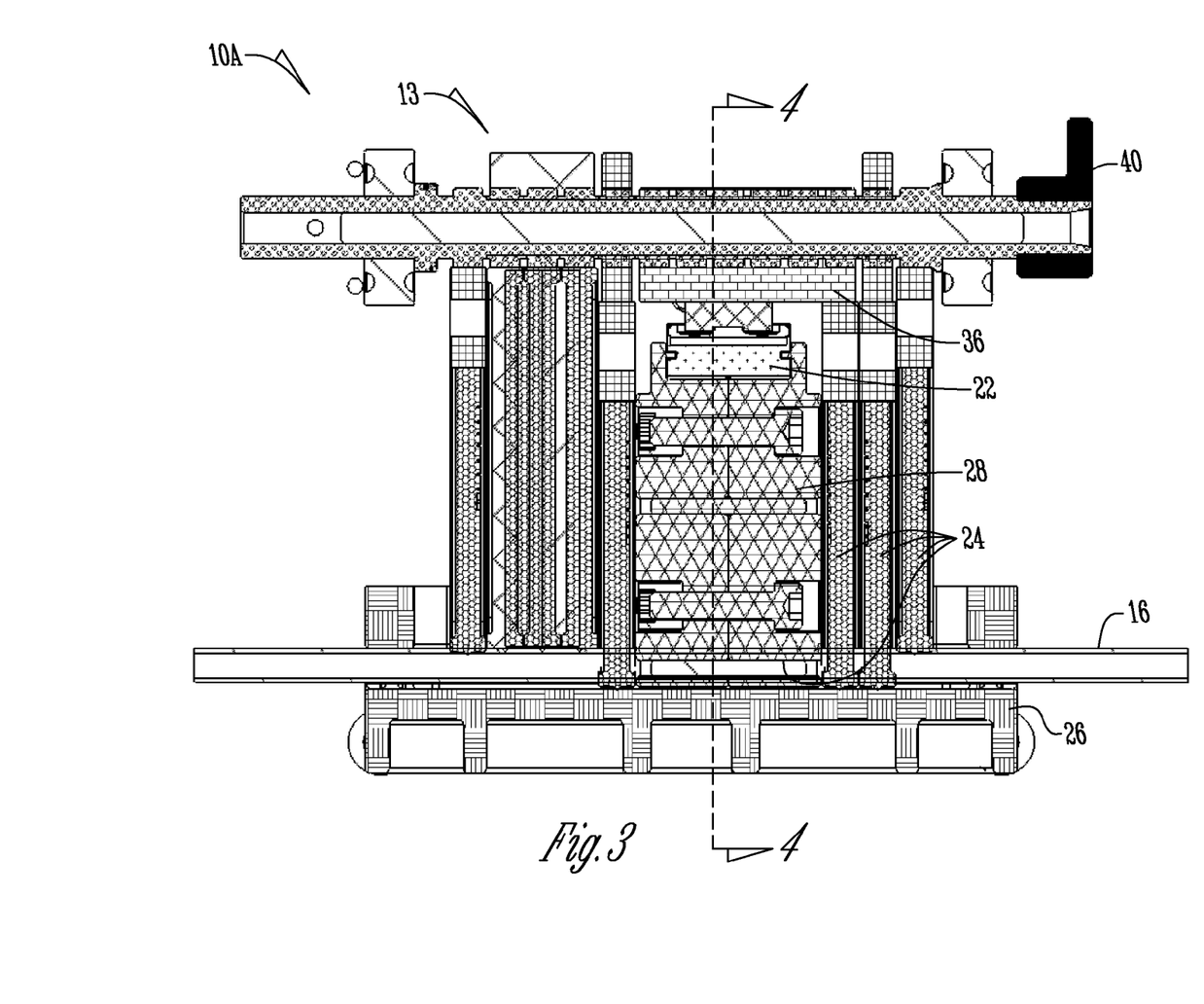
FIG. 3 is a sectional view of a pump system utilized in the present invention.
Figure 4:
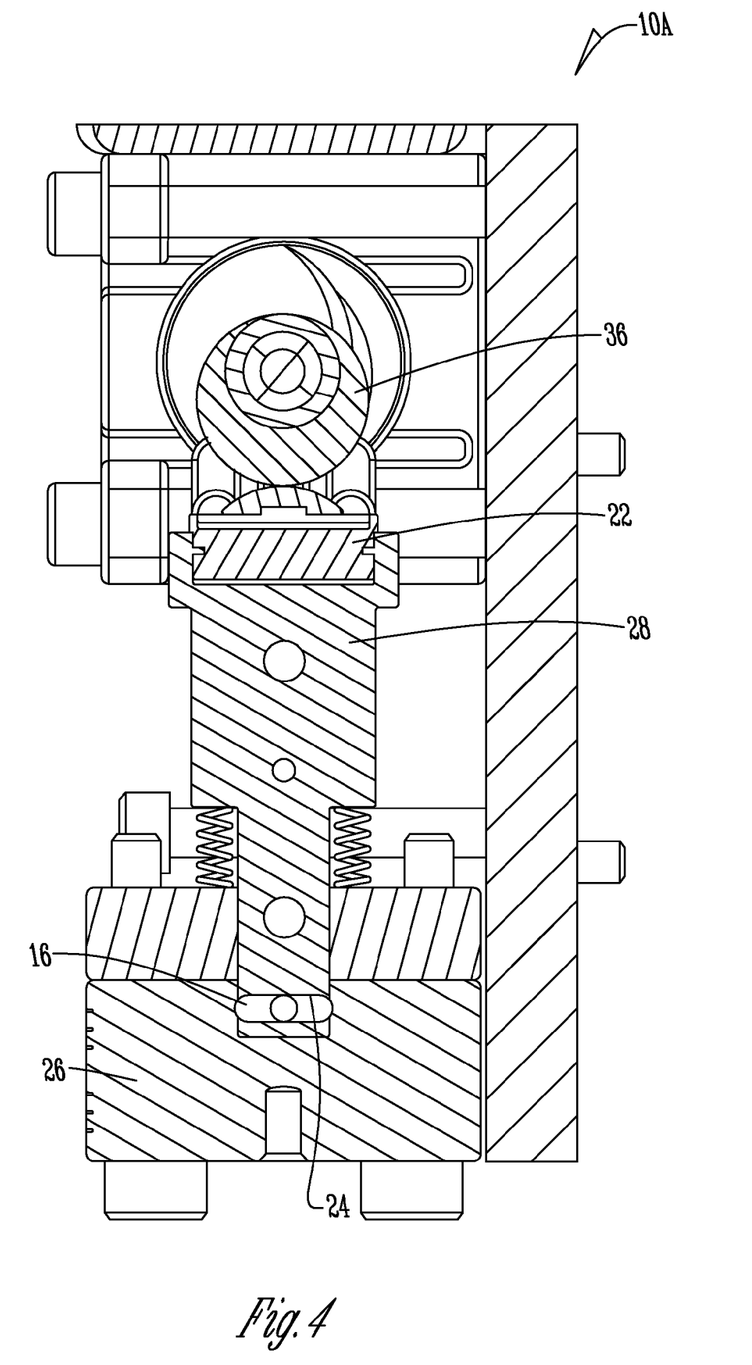
FIG. 4 is a cross sectional view of the pump system taken along line 4-4 in FIG. 3.

FIG. 2A is a graph of tubing compression force data from lab tests providing displacement of an actuating device that moves a force sensor against tubing on the X axis versus load on the Y axis for various tubing samples having a second given set of nominal outside and inside diameters that are different than those depicted in FIG. 2, with and without fluid present in the tubing. In FIG. 2A, the second given set of nominal outside and inside diameters of the tubing includes an outside diameter of 0.170 inches, which is larger than the outside diameter of the tubing in FIG. 2, and an inside diameter of 0.120 inches, which is larger than the inside diameter of the tubing in FIG. 2. In general, the same load versus displacement behavior shown in FIG. 2 is also evident for this size tubing. The only significant differences are that the distance to contact the tubing is less (about 0.010 inches) and the force and distance to occlude the larger size tubing (FIG. 2A) is greater than that of the smaller size tubing (FIG. 2). The curve on the far right of FIG. 2A again represents a run with no tubing in place. That run was done merely to verify the testing setup, wherein the actuator was positioned 0.180 inches from the hard stop surface that normally provided the resting surface for the tubing.

When pumping is first started the position of the touch can determine the outer diameter 20 of the tubing 16. The position of the sharp rise determines the doubled wall thickness (2*t) of the tubing 16, which in turn gives the inner diameter 18 of the tubing 16 according to the formula ID=OD−2t. The slope of the sharp rise gives information on the modulus of the tubing material. During pumping, the position of the first touch can determine if the tubing 16 is ovaling, the position of the sharp rise again determines the wall thickness and inner diameter 18, and the slope at the rise determines the modulus.

Figure 5:
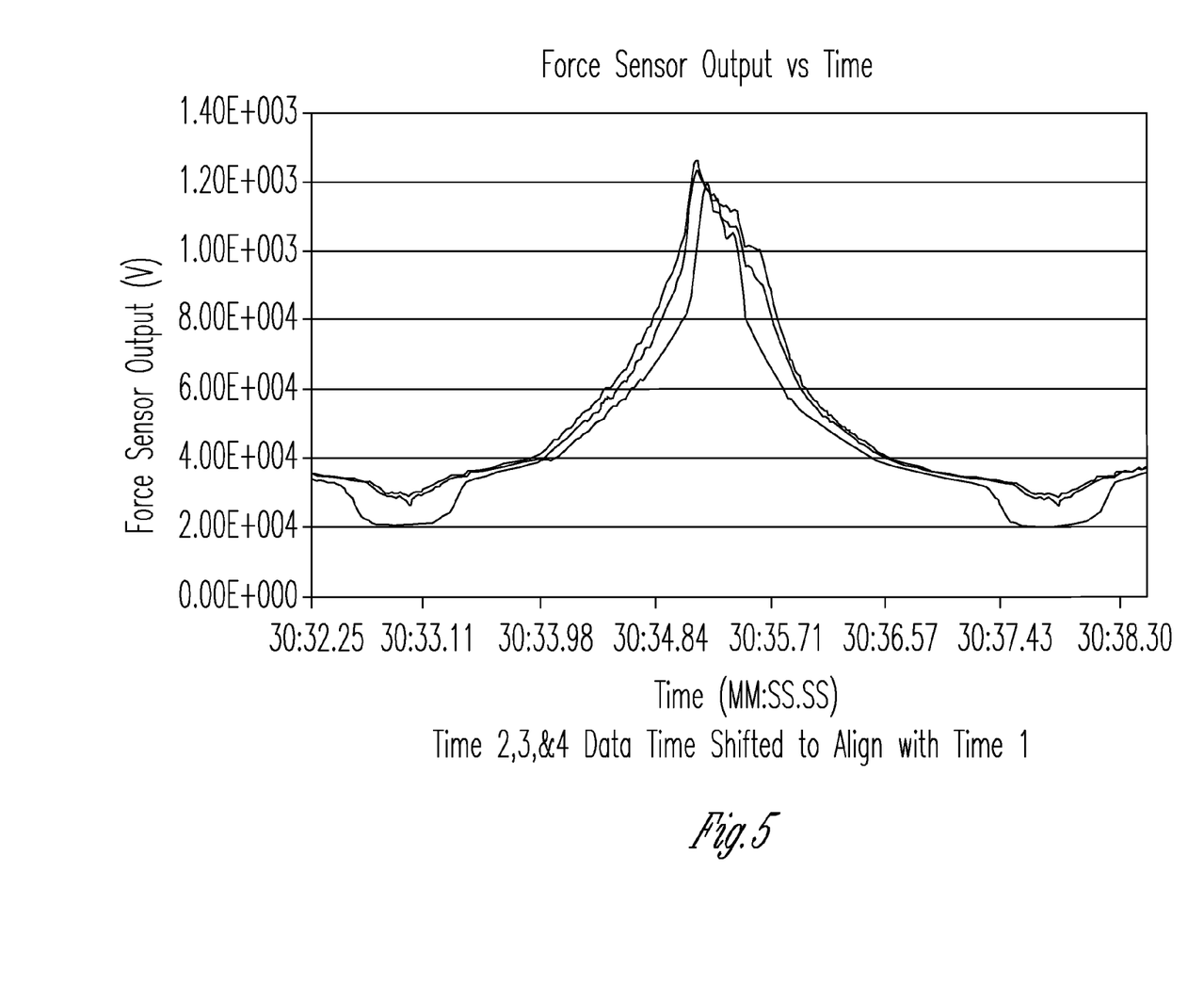
FIG. 5 is a graph of force sensor output versus time for individual pumping stroke cycles, with time on the X axis and force sensor output in voltage on the Y axis, and with each trace representing data taken for a different pump stroke cycle at various times throughout the test but overlaid with each other to show changes in the force sensor output over time.

FIG. 5 is a graph of force sensor output versus time for individual pumping stroke cycles, with time on the X axis and force sensor output in voltage on the Y axis, and with each trace representing data taken for a different pump stroke cycle at various times throughout the test but overlaid with each other to show changes in the force sensor output over time. This graph indicates that the force sensor output voltage decreases as the cycles progress over time and the tubing degrades due the repeated pump strokes.

Alternatively the pressure inside the tubing 16 is measured with a force sensor 22 to detect proximal and distal occlusions. Similarly the modulus can be measured to recognize different tubing material. Tables in the pump controller 14 provide modulus information for different tubing 16, tubing material, or tubing dimensions, etc. for comparison or identification purposes.

The force sensor based embodiment of the invention described above offers several advantages including that it provides a low cost and flexible solution for a disposable device. The pump 12 can use tubing with loose tolerances or different size tubing without sacrificing accuracy. Another advantage is that this system does not require any components be added to the fluid line that would impede flow or create any sterility issues for drug delivery/medical fluid applications. Thus improved flow accuracy over extended times can be provided by this low cost solution. The system has the ability to improve pump flow inaccuracies due to manufacturer's variability in tubing size. This also allows tubing 16 to have larger tolerance and be cheaper to manufacture. This system 10 also provides the ability to distinguish between different sizes of tubing and adjust the speed of the motor of the pump as needed to achieve the desired flow rate. Thus improved pump flow rate control is provided.

Another embodiment of the present invention is applicable to numerous concepts related to fluid flow, including the measurement of fluid flow rate change as applied to medication delivery to the body and potentially to identification of fluid type (liquid, air) that is delivered to patients via IV administration sets. The infusion system 100 of this embodiment of the present invention, as described below and shown by FIGS. 6-9, utilizes electromagnetic characteristics of the tubing itself. Specifically, electrical property data is used to correlate the tubing condition to flow properties and pump performance, and compensate accordingly. A typical peristaltic pump tubing material begins to change during pumping due to environmental and mechanical degradation. It has been observed that over time, the pump output changes due to these conditions. The invention captures and measures directly how such tubing changes impact the pump output among other flow parameters.

Electrical properties of conductive polymer composites are somewhat complex. These properties are affected significantly by temperature, particle size, shape, material constituent, internal stresses, and hydration effects to name a few. However, as a first approximation, a model based on percolation theory holds well to describe the behavior. This follows a power law given by $$\rho = (v - v_c)^{-t}$$

Where, v is the volumetric % of the conductive material in the electrical composite material and $v_c$ is its value at the percolation threshold. The relationship for a particular polymer composite can be determined from the equation $(\rho - \rho_c) = (v - v_c)/(100 - v_c)$.

Such a construct shows that the resistivity of a composite material is a function of particle shape, orientation and dispersion within the matrix. From this, it follows that upon mechanical loading and/or breakdown of the polymer matrix, one can expect that the resistivity (electrical property) of the material to be impacted.

When the concentration of conductive particles is very low, there are no connected pathways for electrical conduction that penetrate or percolate entirely through the composite, and the resistivity of the composites remains infinitely high. As the conductor concentration increases, a point is attained (called the percolation threshold) at which the first connected conductive pathway extending through the composite is constructed. Further increasing the conductor concentration forms more connected pathways, and the resistivity decreases as the conductor concentration increases.

In the percolation model, the resistivity, ρ, of a conducting composite is predicted by:

$$\rho_m = ((z-2)\rho_c\rho_p)/(A + B + [(A+B)^2 + 2(z-2)\rho_c\rho_p)]^{1/2})$$

where $$A = \rho_c[-1 + z/2(1 - f_c/f)]$$

$$B = \rho_m[zf_c/2f - 1]$$

and $\rho_m$ is the resistivity of composite mixture, $\rho_c$ is the resistivity of the low resistance (carbon black) phase, $\rho_p$ is the resistivity of the high resistance (polymer) phase, z is the coordination number of the conductive filler particles, $f_c$ is the critical volume fraction of the low resistance (carbon) component (or percolation threshold), and f is the volume fraction of the low resistance (carbon) phase.

In the infusion system 100 of this embodiment of the invention, at least the portion or section of the tubing 16 that is acted upon by the pumping mechanism 13 during the pumping of fluid or the entire tubing 16 utilized is a conductive polymer composite (CPC) made of electrical materials 60 (not shown) that are embedded, attached to or adhered to a polymer. The CPC tubing 16 may be created by a number of processing steps including mixing, blend, extrusion, vapor deposition, post-process assembly or the like. Such CPC tubing 16 is commercially available from E-Song America of Seoul, Korea.

The pump 12 of this embodiment includes an actuator motor 9 of which may be any type including stepper, servo, dc, etc.). The pump 12 also consists of a basic pumping mechanism 13 that may include gears, cams, camshafts, followers (i.e. pumping fingers), and a chassis. It is neither pertinent nor relevant to this invention to discuss the other myriad of configurations that this pumping system could include. Furthermore, the invention disclosed here within pertains to pressure based pumping systems. It is obvious to one skilled in the art that this invention relates to any one of many such pumping systems, including linear peristaltic, rotary peristaltic, active valve diaphragm pumps, passive valve diaphragm pumps, to name a few.

This embodiment provides tubing 16 that is a polymer conductive tubing material such as a carbon-doped silicone. A tubing 16 or the like may have a base polymer matrix of silicone, PVC, polyethylene, or the like. The conductive ingredient may be carbon, copper, gold, etc. or any other known electrically conductive element, alloy or substance in any state (solid liquid or gas). Further, the conductive element of the tubing system may be embedded, adhered, bonded, fastened, or any similar means to the internal or external tubing surfaces. Further, the tubing 16 may be in any shape or form such as rectangular, square, oval or the like. In an alternate embodiment, the tubing 16 may be in a hollow cylinder or flat sheet (membrane) form.

Figure 6:
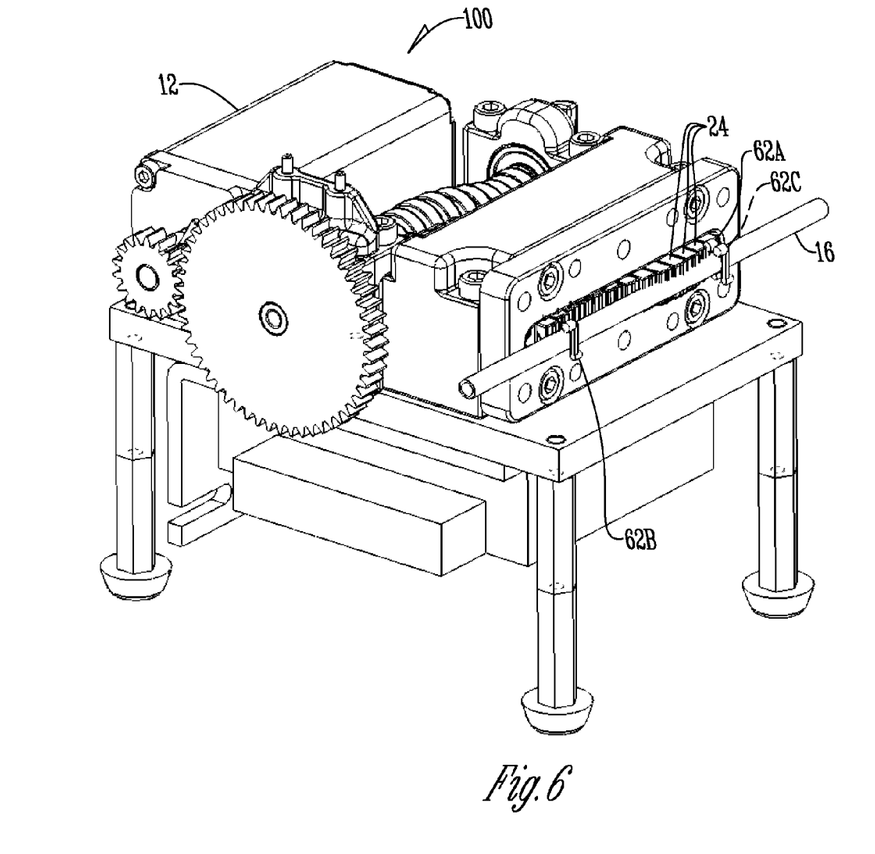
FIG. 6 is a perspective view of another embodiment of the present invention.

The infusion system 100 of the embodiment shown in FIG. 6, also includes a plurality of spaced electrodes 62 (or more precisely 62A, 62B or 62A, 62C or 62B, 62C, etc.) that operatively contact the electrically conductive portion of the tubing 16 so as to provide an electric signal indicative of at least one electrical property of the tubing 16. The electrodes 62 allow the system to sense, measure, analyze and record electrical property information of the tubing 16. The electrodes 62 may directly or indirectly contact or engage the tubing 16 or be embedded therein. Similarly the electrodes 62 may be presented in any of a number of mounting configurations or arrangements with respect to the tubing 16. The important aspect is that the electrodes 62 are spaced apart with at least a portion of the tubing 16 operatively interposed therebetween for measurement or sensing purposes. The electrodes 62 can be mounted in a housing 64 or a door 66 (both of which are removed and not shown in FIG. 6) of a peristaltic pump 12 and can be located adjacent to the tubing 16 and spaced apart along the length of the tubing 16. In other words, the electrodes 62 can be arranged axially with respect to a longitudinal axis of the tubing 16 or parallel to the longitudinal axis of the tubing, as illustrated by 62B, 62C in FIG. 6. Alternatively the electrodes 62 can be located adjacent to the tubing 16 in a plane that is transverse, perpendicular or skewed with respect to the longitudinal axis of the tubing 16. For example, the electrodes 62 can be arranged transversely with respect to a longitudinal axis of the tubing 16, as illustrated by 62A, 62C or 62A, 62B in FIG. 6. One or more of the electrodes, such as electrode 62A for example, can be connected to, attached to or integrated into the end of one of the fingers 24 of the pumping mechanism 13. In particular, when the electrodes 62 are radially spaced around a circumference of the tubing 16 or on opposite sides of the tubing 16, as illustrated by 62A, 62C in FIG. 6, electrical properties or information about the fluid contents of the tubing can also be determined.

The electrodes 62 may be made of a number of shapes, circular, tubular, rectangular and the like. The electrodes 62 may also be made of any conductive material including copper, brass, gold and the like. The electrodes 62 can also be permanently attached, removably attached, embedded, separate from CPC tubing 16 or the like. For the purpose of measurement effectiveness the electrodes 62 may be placed in a number of various configurations or combinations of configurations, such as discussed above and any number of electrodes 62 (two or more) can be utilized at any one time.

In a preferred embodiment the electrodes are thin flat stock copper, gold or the like. The electrode 62 may be of one of several different configurations including malleable sheets, foils, tapes, wires or the like. The shape and contact of the electrodes may be that of circular, oblong (oval), rectangular, triangular, coiled, etc. The electrode contact area may be that of a point, flat rectangular, flat circular, cylindrical (i.e. pogo pins) etc. The electrodes 62 may be embedded in the tubing materials, glued, soldered, taped, mechanically attached, etc. to the tubing surface wall. Alternatively, the electrodes 62 may be mounted within the pump zone in any number of ways to the pumping fingers, door assembly, etc.

The system 100 can optionally include a measurement system 68 (not shown) such as a digital multimeter (DMM) that is in electrical communication with the electrodes 62 to capture, process, measure and optionally display electrical information and measurement such as impedance, resistivity, conductivity or the like. The measurement system 68 in one embodiment is a Digital Multi Meter (DMM). Other embodiments of this measuring system 68 may be a voltmeter, ohmmeter, electrical resistance sensor, or resistance sensing circuit PCBA. Alternatively, the measuring system 68 and its functions can be integrated into the controller 14.

The controller 14, and the measurement system 68 if provided, and electrodes 62 are connected to one another via electronics 70 that may be hard-wired, wireless, optical or the like. The electronics 70 that communicate with the system 100 may be remote from or integrated with the CPC tubing 16. Electronics 70, for the purpose of measuring electronic signals, may include any of amplification, signal conditioning, analog to digital conversion and power conversion. In a preferred embodiment the measurement system 68 and/or controller 14 for commercial applications would include those that are typical in current day electronics (i.e., sensing circuits within PCBAs, microcontrollers and other electronic components including electrical resistance sensors).

In operation, as fluid flows through the tubing 16 electrical characteristics or information of the tubing 16 are monitored via the electrodes 62 and measured by the measurement system 68 or controller 14 that electrically communicates with the electrodes 62. Specifically, electrical information of the CPC tubing 16, or tubing 16 with conductive constituents, or tubing 16 with a conductive component coupled therewith is monitored, including in alternative embodiments the form of other geometries including membranes, sheets or non-circular tubing. Specifically electrical information in the form of impedance, resistivity, conductivity or the like is provided.

The electrodes 62 communicate their signal indicative of the electrical information from the tubing 16 to the measurement system 68 or controller 14 of the pump 12 via electronics 70 wherein the controller 14 utilizes an algorithm, as discussed with regard to the first embodiment, and adjusts the fluid flow accordingly. The algorithm to determine precise flow rate variances from the monitor output could be resident in the controller 14 on the pump 12, in a remote memory or processor, or elsewhere depending on the application.

Alternatively, instantaneous electrical information can be measured and communicated about the tubing 16 or fluid (gas or liquid) inside the tubing 16 to predict occlusions, air-in-line, particles or other flow events. Alternatively, sensors or other means may be utilized for measuring or capturing electrical information.

Figure 7:
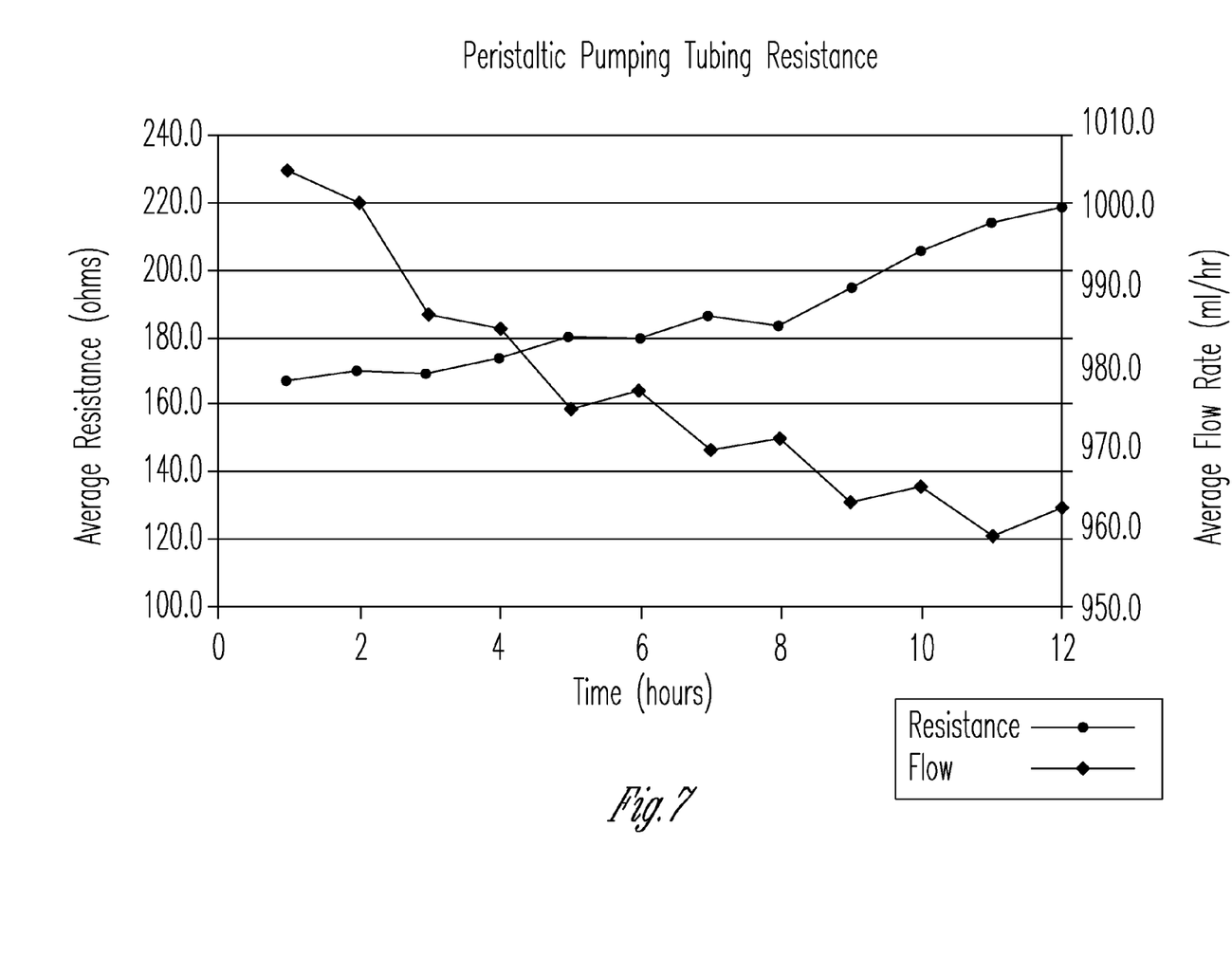
FIG. 7 is a graph of tubing resistance with time on the X axis and average resistance in ohms on the Y axis also shown with average flow rate on another Y axis for the configuration shown in FIG. 6 where the electrodes are placed or spaced axially along the length of the tubing and on the same side thereof.
Figure 8:
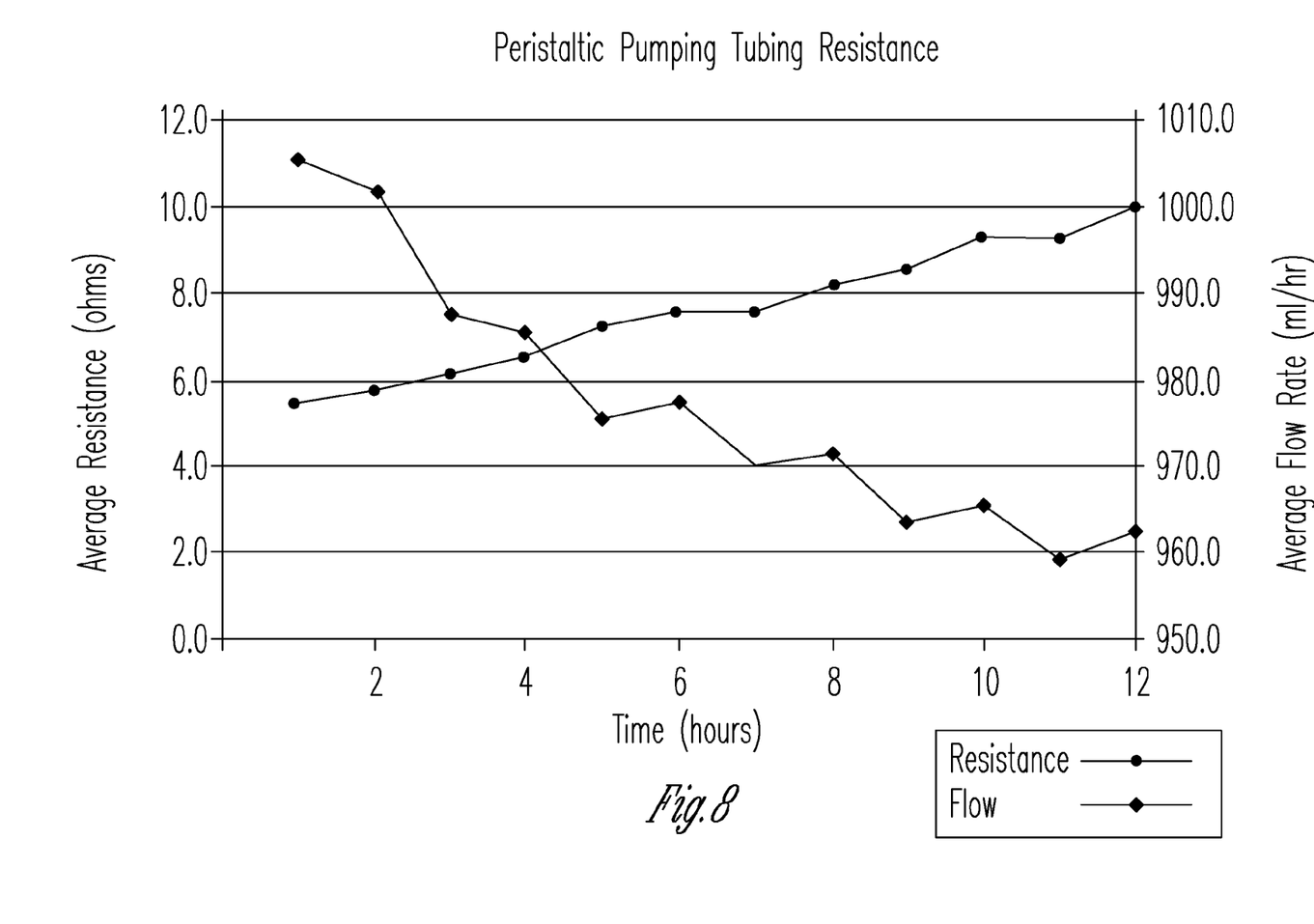
FIG. 8 is a graph of tubing resistance with time on the X axis and average resistance in ohms on the Y axis also shown with average flow rate on another Y axis for the configuration shown in FIG. 6 where the electrodes are placed or spaced transversely, more particularly radially, with respect to the longitudinal axis of the tubing.

Attached as FIGS. 7 and 8 are graphs showing two electrical resistance values simultaneously obtained utilizing this particular embodiment of the system 100 during a run for twelve hours of continuous pumping at a constant motor speed of room temperature water in an uncontrolled temperature/humidity environment. The graph of FIG. 7 depicts resistance and flow rate data from the parallel to the tubing or axial electrode arrangement 62B, 62C shown in FIG. 6 while the graph of FIG. 8 depicts resistance and flow rate data from the transverse or more particularly perpendicular, radial electrode configuration or arrangement 62A, 62C shown in FIG. 6. Perhaps due to the relatively large distance between the electrodes 62B, 62C, the resistance is greater in FIG. 7 than FIG. 8.

From the two graphs it is evident that there is a relationship between the CPC tubing measurement and diminishing flow rate over time. That is, over time as the tubing 16 begins to physically wear and change, the intrinsic resistivity of the tubing 16 changes as well. In particular, an inverse relationship observed and the flow rate decreases over time as the tubing 16 begins to degrade while the resistivity increases over the same time span. The electrical conductivity of the tubing, which is inversely related to its resistivity, therefore is directly related in a positive manner to the flow rate. The conductivity of the tubing decreases over time or with repeated use and the fluid flow rate also tends to decrease or fall off over time. As such, tubing electrical properties that are easily measured as described herein can be used to monitor, control, and operate a pump to run at constant flow rate. In the case of cylindrical tubing 16 the electrodes 62 could be transversely arranged, or more preferably radially spaced around the circumference of the tubing 16. The electrodes 62 can be disposed on opposing sides of the tubing 16 or on the same side. The electrodes 62 can be skewed at an angle with respect to each other. The important thing is that they must be spaced apart to provide a meaningful signal and that an electrically conductive portion of the tubing 16 that is at least in part acted upon by the pumping mechanism 13 during the pumping of fluid through the tubing is operatively contacted by the electrodes. If more of the tubing 16 is electrically conductive, greater flexibility in mounting the electrodes with respect to the pumping mechanism 13 can be achieved. For example, if the electrically conductive portion of the tubing 16 extends beyond the pumping mechanism 13, one or more of the electrodes 62 can engage said conductive portion of the tubing remote from the pumping mechanism.

As shown in FIG. 8 the transverse electrode configuration has the electrodes 62A, 62C positioned such that a composite resistivity of the tubing and fluid media is obtained. In this configuration (transversely mounted), the type of liquid in the tubing 16 can be detected or determined. Because gas (air) has a very high electrical resistivity or low electrical conductivity relative to most liquids, the signal yields information regarding the fluid. That is, this configuration is ideal for being able to detect air bubbles, voids or leaks within fluid conduits and their contents.

Other configurations are possible that yield new information regarding tubing deformation, flow parameters, and pump performance. Circumferential electrodes 62, spaced very closely apart can give specific information regarding local deformation changes over time. The signals, for instance, can be integrated to show how a cross section of tubing changes over time. Further electrode geometries are possible including axial skewed, offset, coaxial, etc. Utilizing any of these configurations provides a signal carrying information or data about the tubing and pump performance.

The system 100 described above provides a method of controlling of an infusion pump system based upon an electrical property of the tubing 16. The method comprises the steps of: 1) providing a tubing 16 having an electrically conductive portion adapted to be operated upon by a pumping mechanism 13; 2) monitoring an electrical property of the electrically conductive portion of the tubing while said portion is being operated on by the pumping mechanism 13; and 3) controlling the operation of the pumping mechanism 13 to adjust the fluid flow rate of the infusion pump system based upon the monitored electrical property. The step of controlling the operation of the pumping mechanism 13 can include adjusting the speed of the pumping mechanism, the position or depth of travel of one or more of the pumping fingers or the like. The typical electrical properties or characteristics of a given type of tubing to be used or the specific tubing 16 used can be determined in advance and correlated with the fluid flow rate or performance of the infusion system over a period of time. This can be accomplished through testing at the factory of the infusion system manufacturer or during a break in or test period prior to or during actual use of the infusion system 100 by the end user. Prior to the controlling step, an electrical property related to the electrical conductivity of the tubing 16 is correlated with a fluid flow parameter by monitoring the electrical property and the fluid flow parameter over a plurality of pumping test cycles that occur in a given time period at a given speed of the pumping mechanism 13 and begin with a given nominal value of the fluid flow parameter.

As mentioned above, the system 100 is also useful for determining if an alarm should be generated for various undesirable conditions that can occur in the infusion system. By monitoring and determining if an electrical property has changed in excess of predetermined value and activating an alarm if the determination is positive the user can be warned of such conditions. The predetermined value can be an increase or decrease by a given amount of an electrical property of the tubing or the predetermined value can be defined as a given rate of change that would trigger the alarm. As discussed above, with certain electrode configurations, the resistivity increases greatly and the conductivity decreases greatly in the tubing 16 when gas or air bubbles are present in the fluid media within the tubing. Thus, an alarm indicating the presence of air in line can be generated based upon the electrical property of the tubing and the fluid it contains.

In general, the system 100 provides a method for compensating for degradation of the fluid flow rate over time and a plurality of repetitive pumping cycles. The controller 14 adjusts the operation of the pumping mechanism 13 to increase the fluid flow rate when the monitored electrical conductivity decreases so as to compensate for degradation of the tubing.

Thus, several advantages are presented. The system 100 can accurately calculate how the flow rate of the pump 12 is changing in view of sensed tubing material changes. As mentioned, these changes may be due to any number of independent factors or a combination of interrelated factors. Therefore, the system can be used to correct for varying flow rates typically encountered in the complex clinical environment.

Other advantages include a low cost solution particularly for a disposable system because only a small amount of conductive materials (e.g. carbon black) needs to be added into any number of polymer matrices and still use the exact same tube manufacturing processes and techniques that are presently employed. Another advantage is that the invention does not require any components to be added to the fluid line that would impede flow or create any sterility issues for drug delivery or medical fluid applications. Another advantage is that the measurement method for detecting flow rate/tubing wear changes is less complex than other methods because it relies on measuring a single, easy to measure feature of the tubing 16. Thus, the system 100 improves flow accuracies and can provide additional functionalities such as air-in-line, sensing inline disconnection or failure by leaking. This system has the ability to improve pump flow inaccuracies that are due to the disposable tubing set degrading over time. The system also allows generic tubing sets to be used in conjunction with any given pump. Thus, at the very least all of the stated objectives have been met.

It will be appreciated by those skilled in the art that other various modifications could be made to the device without departing from the scope of this invention. All such modifications and changes fall within the scope of the claims and are intended to be covered thereby.

What is claimed is:

1. An infusion pump system comprising:
a pumping mechanism for pumping fluid through tubing;
a controller connected to the pumping mechanism for controlling the pumping mechanism and a flow rate of fluid through tubing;
said tubing having at least a first portion that is electrically conductive and is at least in part acted upon by the pumping mechanism during the pumping of fluid through the tubing;
a plurality of spaced apart electrodes operatively contacting the first portion of the tubing so as to provide an electric signal indicative of at least one electrical property of the tubing; and
wherein the controller adjusts the pumping mechanism in response to the electric signal and varies the flow rate of the fluid through the tubing as a result of the electric signal.

2. The infusion pump system of claim 1 wherein the pumping mechanism is a peristaltic pump.

3. The infusion pump system of claim 1 wherein the first portion of the tubing includes a composite polymer conductive material.

4. The infusion system of claim 3 wherein the composite polymer conductive material is a carbon-doped silicone.

5. The infusion system of claim 1 wherein the electrodes are embedded in the tubing.

6. The infusion system of claim 1 wherein the electrodes are arranged axially with respect to a longitudinal axis of the tubing.

7. The infusion system of claim 1 wherein the electrodes are transversely arranged with respect to a longitudinal axis of the tubing.

8. The infusion system of claim 7 wherein the electrodes are radially spaced around a circumference of the tubing.

9. The infusion system of claim 1 wherein the at least one electrical property of the tubing is selected from a group of electrical properties consisting of resistivity, conductivity and impedance.

10. The infusion system of claim 1 wherein the controller is connected to a motor drivingly coupled to the pumping mechanism and adjusts the speed of the motor in response to the electric signal.

11. The infusion system of claim 1 wherein the electrodes provide the electric signal over time so as to include a plurality of pumping cycles and the controller adjusts the flow rate based on a change in the electric signal over time.

12. The infusion system of claim 1 further comprising a measuring system electrically connected to the controller and to the electrodes to process and measure the electric signal provided by the electrodes.

13. The infusion system of claim 12 wherein the measuring system is a digital multimeter.

14. A method of controlling of an infusion pump system, comprising the steps of:
    providing a tubing having an electrically conductive portion adapted to be operated upon by a pumping mechanism;
    monitoring an electrical property of the electrically conductive portion of the tubing while said portion is being operated on by the pumping mechanism; and
    controlling the operation of the pumping mechanism to adjust a fluid flow rate of the infusion pump system based upon the monitored electrical property.

15. The method of claim 14 wherein the step of controlling the operation of the pumping mechanism includes adjusting the speed of the pumping mechanism.

16. The method of claim 14 further comprising the step of, prior to the controlling step, correlating an electrical property related to the electrical conductivity of the tubing with a fluid flow parameter by monitoring the electrical property and the fluid flow parameter over a plurality of pumping test cycles that occur in a given time period at a given speed of the pumping mechanism and begin with a given nominal value of the fluid flow parameter.

17. The method of claim 14 further comprising the substeps during the monitoring step of: determining if the electrical property has changed in excess of predetermined value; and activating an alarm if the determination is positive.

18. The method of claim 17 wherein the predetermined value is one of a given amount and a given rate of change.

19. The method of claim 17 wherein the activating alarm substep includes activating an air in line alarm.

20. The method of claim 14 wherein when the monitored electrical property is conductivity and the conductivity decreases, the fluid flow rate is adjusted to increase so as to compensate for degradation of the tubing.

* * * * *